(12) United States Patent
Khan et al.

(10) Patent No.: US 8,304,544 B2
(45) Date of Patent: Nov. 6, 2012

(54) PALONOSETRON FREE BASE AND PROCESS FOR ITS PREPARATION

(75) Inventors: Mubeen Khan, Navi Mumbai (IN);
Mahendra Patil Raghunath, Dhule (IN); Prashant Yadav Kundlik, Thane (IN)

(73) Assignee: Glenmark Generics Limited, Mumbai (IN)

( * ) Notice: Subject to any disclaimer, the term of this patent is extended or adjusted under 35 U.S.C. 154(b) by 242 days.

(21) Appl. No.: 12/746,768

(22) PCT Filed: Dec. 11, 2008

(86) PCT No.: PCT/IN2008/000833
§ 371 (c)(1),
(2), (4) Date: Jun. 8, 2010

(87) PCT Pub. No.: WO2009/087669
PCT Pub. Date: Jul. 16, 2009

(65) Prior Publication Data
US 2010/0292267 A1    Nov. 18, 2010

Related U.S. Application Data

(60) Provisional application No. 61/062,479, filed on Jan. 25, 2008.

(30) Foreign Application Priority Data

Dec. 13, 2007 (IN) .................. 2448/MUM/2007

(51) Int. Cl.
*C07D 453/02* (2006.01)
(52) U.S. Cl. ......................................................... 546/99
(58) Field of Classification Search ................. None
See application file for complete search history.

(56) References Cited

U.S. PATENT DOCUMENTS

| | | | |
|---|---|---|---|
| 5,202,333 A | 4/1993 | Berger et al. | |
| 5,510,486 A | 4/1996 | Robinson, III et al. | |
| 5,567,818 A | 10/1996 | Kowalczyk et al. | |

FOREIGN PATENT DOCUMENTS

| | | |
|---|---|---|
| EP | 0430190 A1 | 5/1991 |
| WO | 2008/146283 A2 | 12/2008 |
| WO | 2009010987 A1 | 1/2009 |
| WO | 2009136405 A1 | 11/2009 |

OTHER PUBLICATIONS

Bruce A. Kowalczyk and Norman H. Dyson, "Hydrogenation of a Chiral 1H-Benz[de]isoquinolin-1-one and an Equilibration Using Palladium catalyst", Organic Process Research & Development 1997 1 (2), 117-120.

*Primary Examiner* — Janet Andres
*Assistant Examiner* — Timothy R Rozof
(74) *Attorney, Agent, or Firm* — Louisa Lao (57) ABSTRACT

The present invention provides novel palonosetron free base in an amorphous form and crystalline form-G and processes for their preparation. The present invention also provides a process for the preparation of palonosetron hydrochloride from the novel palonosetron free base in an amorphous form and/or in crystalline form-G.

8 Claims, 9 Drawing Sheets

PALONOSETRON FREE BASE AND PROCESS FOR ITS PREPARATION

PRIORITY

This application claims the benefit under 35 U.S.C. §119 to U.S. provisional application No. 61/062,479 filed on Jan. 26, 2008 and to Indian Provisional Application No. 2448/MUM/2007 filed on Dec. 13, 2007, entitled "PALONOSETRON FREE BASE AND PROCESS FOR THE PREPARATION OF THE SAME", the contents of which are incorporated by reference herein.

BACKGROUND OF THE INVENTION

1. Technical Field

The present invention generally relates to an isolated palonosetron free base, substantially in a solid amorphous form, processes for its preparation, a process for its conversion into pharmaceutically acceptable salts of palonosetron, and pharmaceutical compositions containing the same.

The present invention also provides a palonosetron free base of crystalline form-G, a process for its preparation and process for its conversion into a pharmaceutically acceptable salt thereof; and pharmaceutical compositions containing the same.

2. Description of the Related Art

Palonosetron, also known as (3aS)-2-[(S)-1-azabicyclo[2.2.2]oct-3-yl]-2,3,3a,4,5,6-hexahydro-1-oxo-1H benz[de]isoquinoline, is represented by the structure of Formula I:

(I)

Palonosetron hydrochloride is an antiemetic and antinauseant agent and is available in the market under the brand name ALOXI® in the form of injection. Each vial contains palonosetron hydrochloride equivalent to 0.25 mg of base.

U.S. Pat. No. 5,202,333 ("the '333 patent") discloses 5-HT3 receptor antagonists such as palonosetron and its hydrochloride salt form. The '333 patent further discloses a process for the preparation of 5-HT3 receptor antagonists palonosetron hydrochloride by reduction of 2-(1-azabicyclo[2.2.2]oct-3-yl)-2,4,5,6-tetrahydro-1H-benz[de]isoquinolin-1-one of formula II (II)

using palladium catalyst in acetic acid and perchloric acid. The intermediate was isolated in a semi-solid which was then converted to a hydrochloride salt.

U.S. Pat. No. 5,567,818 ("the '818 patent") discloses a process for preparing palonosetron hydrochloride by reduction of 2-(1-azabicyclo[2.2.2]oct-3-yl)-2,4,5,6-tetrahydro-1H-benz[de]isoquinolin-1-one using palladium catalyst in toluene and tetrahydrofuran mixture and the resultant palonosetron isolated as its hydrochloride salt. The free base palonosetron was not isolated, but was converted directly into the hydrochloride salt of palonosetron. The '818 patent also discloses reduction of 241-azabicyclo[2.2.2]oct-3-yl)-2,4,5,6-tetrahydro-1H-benz[de]isoquinolin-1-one using palladium catalyst in ethanol and water mixture.

Patent Publication WO2008/146283 (the '283 patent) discloses processes for preparation and purification of palonosetron and salts thereof. The '283 patent discloses isomers of palonosetron designated as Compound A and Compound B.

SUMMARY OF THE INVENTION

The present invention provides isolated palonosetron free base.

The present invention further provides a process for the preparation of isolated palonosetron free base in an amorphous form.

The invention provides a process for a preparation of an isolated palonosetron free base in solid amorphous form which possesses reduced volatile organic solvents.

The present invention provides a process for the preparation of isolated palonosetron free base in solid amorphous form comprising; hydrogenating 2-(1-azabicyclo[2.2.2]oct-3-yl)-2,4,5,6-tetrahydro-1H-benz[de] isoquinolin-1-one of formula-II with a hydrogenation catalyst, in water.

The present invention provides a process for a preparation of an isolated palonosetron free base in solid amorphous form comprising;
 a) hydrogenating 2-(1-azabicyclo[2.2.2]oct-3-yl)-2,4,5,6-tetrahydro-1H-benz[de] isoquinolin-1-one of formula-II with a hydrogenation catalyst, in water;
 b) isolating the palonosetron free base.

The present invention provides a process for a preparation of palonosetron free base in solid amorphous form comprising;
 a) hydrogenating 2-(1-azabicyclo[2.2.2]oct-3-yl)-2,4,5,6-tetrahydro-1H-benz[de] isoquinolin-1-one of formula-II with a hydrogenation catalyst, in water;
 b) isolating the palonosetron free base.
wherein the hydrogenation catalyst is selected from palladium, platinum, nickel, and rhodium.

The present invention provides a process for the preparation of a pharmaceutically acceptable salt of palonosetron free base in solid amorphous form.

The present invention provides a process for a preparation a pharmaceutically acceptable salt of palonosetron free base in solid amorphous comprising;
 a) hydrogenating 2-(1-azabicyclo[2.2.2]oct-3-yl)-2,4,5,6-tetrahydro-1H-benz[de] isoquinolin-1-one of formula-II with a hydrogenation catalyst, in water
 b) isolating the palonosetron free base,
 c) converting the palonosetron free base into its pharmaceutically acceptable salts thereof.

The present invention provides a process for a preparation a pharmaceutically acceptable salt of palonosetron free base in solid amorphous form comprising;

a) hydrogenating 2-(1-azabicyclo[2.2.2]oct-3-yl)-2,4,5,6-tetrahydro-1H-benz[de] isoquinolin-1-one of formula-II with a hydrogenation catalyst, in water
b) isolating the palonosetron free base,
c) converting the palonosetron free base into its pharmaceutically acceptable salts thereof;

wherein the hydrogenation catalyst is selected from palladium, platinum, nickel, and rhodium.

The present invention further provides isolated palonosetron free base in an amorphous form.

The present invention provides an isolated palonosetron free base in solid form.

The present invention also provides palonosetron free base substantially wherein at least about 80% of palonosetron free base is an amorphous form.

The present invention also provides palonosetron free base substantially wherein at least about 90% of palonosetron free base is an amorphous form.

The present invention provides palonosetron free base substantially wherein at least about 95% of palonosetron free base is an amorphous form.

The present invention provides palonosetron free base substantially wherein at least about 99% of palonosetron free base is an amorphous form.

Figure 1:
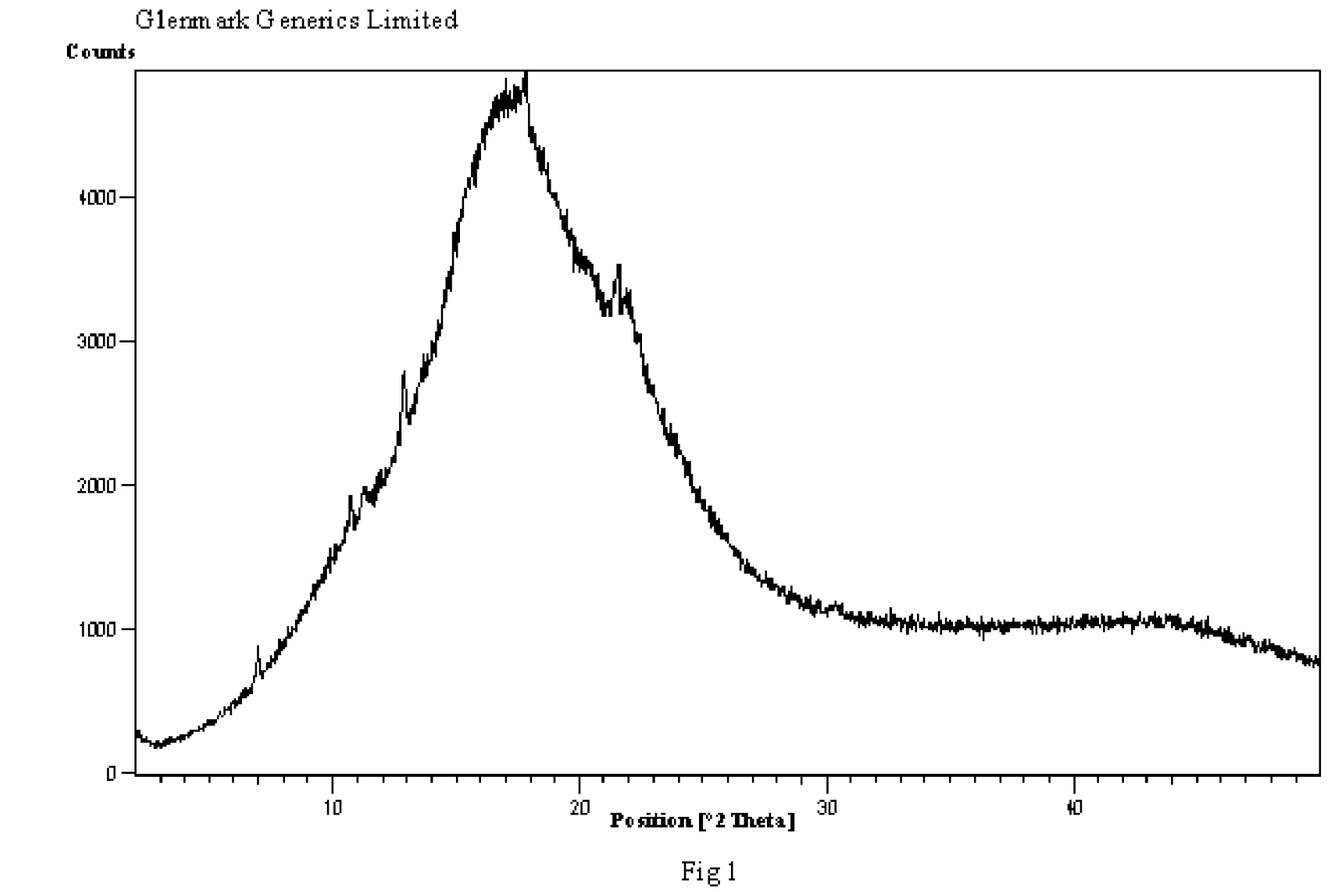
FIG. 1 is a characteristic XRPD of palonosetron free base in an amorphous form.

The present invention provides palonosetron free base in a solid amorphous form characterized by an X-ray powder diffraction pattern (XPRD) substantially in accordance with FIG. 1.

Figure 2:
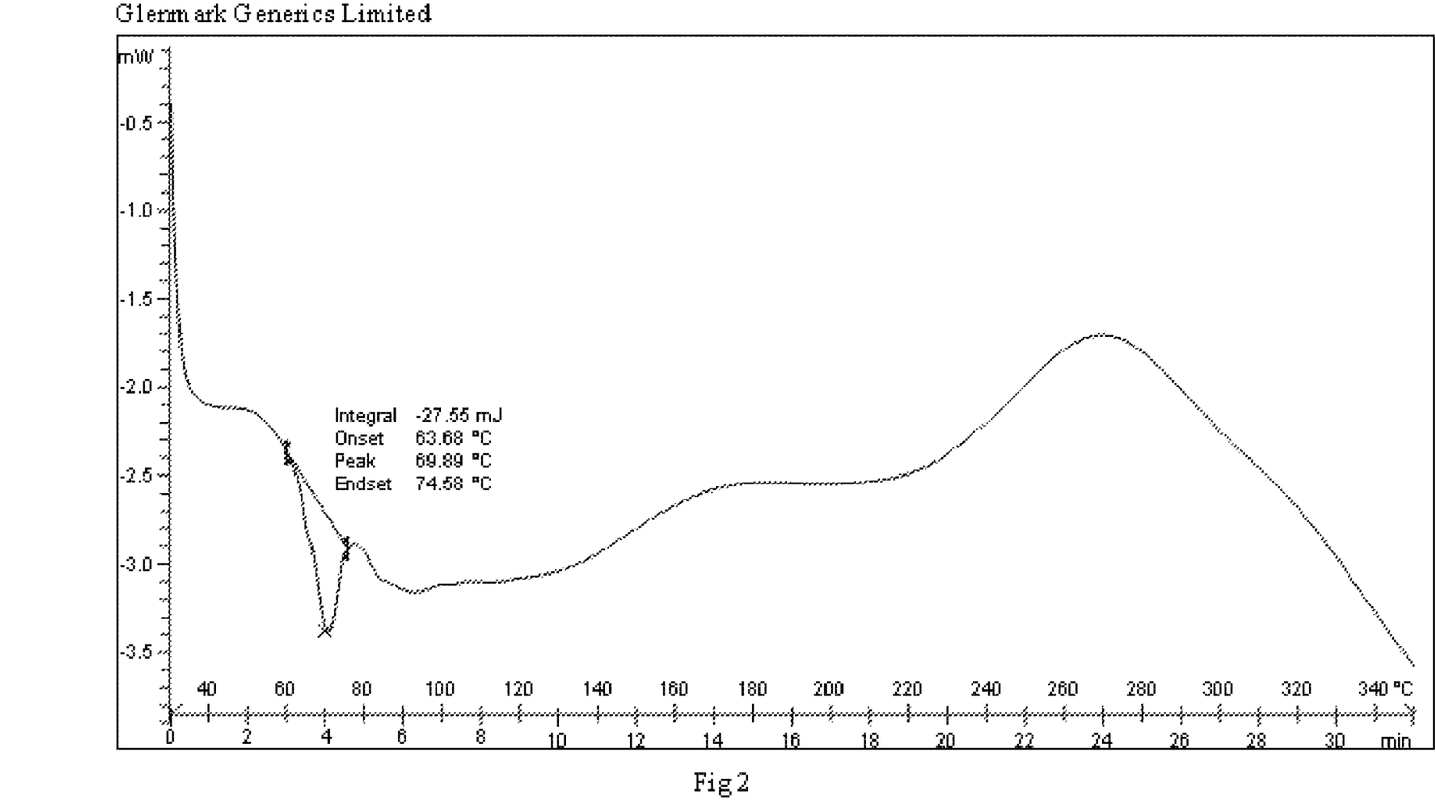
FIG. 2 is a characteristic DSC thermogram of palonosetron free base in an amorphous form.

The present invention provides a palonosetron free base in a solid amorphous form characterized by a differential scanning calorimetric (DSC) thermogram substantially in accordance with FIG. 2.

The present invention further provides a palonosetron free base in crystalline form-G.

Figure 4:
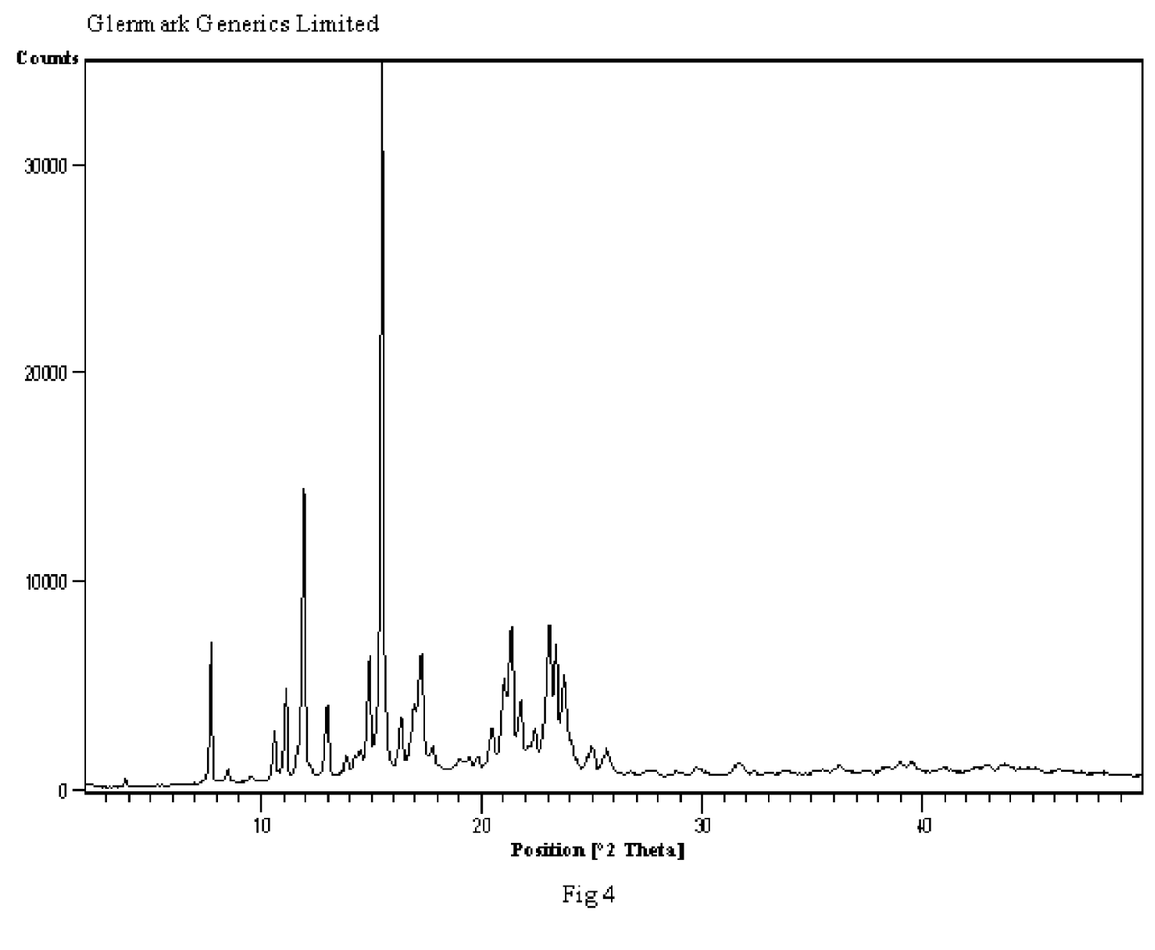
FIG. 4 is a characteristic XRPD of palonosetron free base in crystalline form-G.

The present invention provides a palonosetron free base in crystalline form-G characterized by an X-ray powder diffraction pattern (XPRD) substantially in accordance with FIG. 4.

Figure 5:
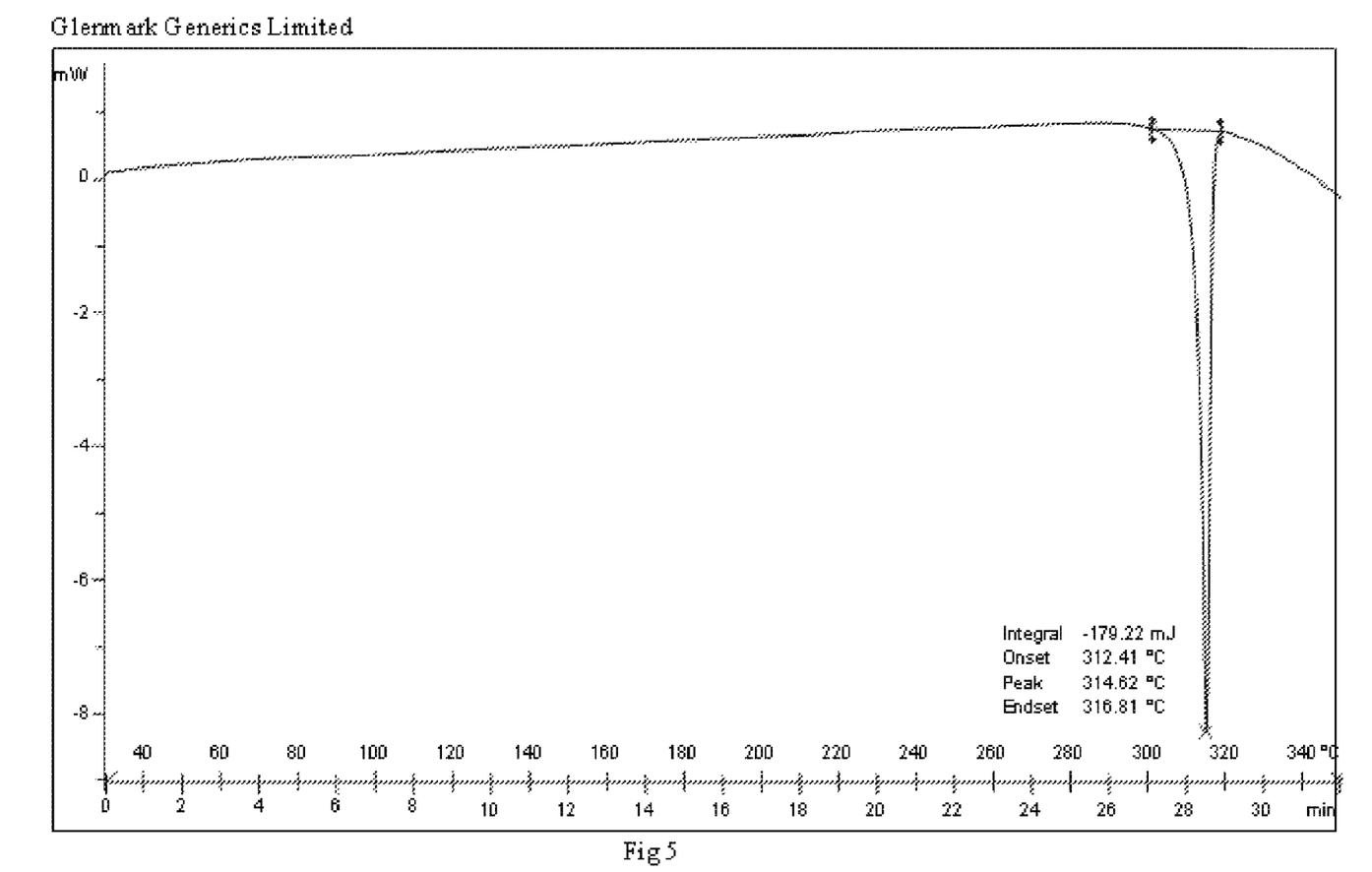
FIG. 5 is a characteristic DSC thermogram of palonosetron free base in crystalline form-G.

The present invention provides a palonosetron free base in crystalline form-G characterized by a differential scanning calorimetric (DSC) thermogram substantially in accordance with FIG. 5.

The present invention provides a process for the preparation of palonosetron free base in crystalline form-G.

The present invention provides a process for the preparation of palonosetron free base in crystalline form-G comprising a) providing a solution of palonosetron or a pharmaceutically acceptable salt thereof, obtained by the processes herein described above in a water immiscible organic solvent and water;
b) treating with a base;
c) concentrating the water immiscible organic solvent; and
d) crystallizing the resultant residue in a suitable organic solvent.

The present invention provides a process for converting a palonosetron free base in crystalline form-G into its pharmaceutically acceptable salts thereof.

The present invention provides a pharmaceutical composition comprising a therapeutically effective amount of a palonosetron free base in an amorphous form or a therapeutically effective amount of a palonosetron free base in crystalline form-G and at least one pharmaceutically acceptable carrier.

DETAILED DESCRIPTION OF THE INVENTION

The palonosetron free base of formula-I of the present invention, or a pharmaceutically acceptable salt thereof (I)

by hydrogenating the 2-(1-azabicyclo[2.2.2]oct-3-yl)-2,4,5,6-tetrahydro-1H-benz[de]isoquinolin-1-one of formula-II with a hydrogenation catalyst, in water.

(II)

The isolated solid palonosetron free base may be substantially in amorphous form which may be converted into a pharmaceutically acceptable salt.

The palonosetron free base in solid, amorphous form is isolated by:

a) hydrogenating 2-(1-azabicyclo[2.2.2]oct-3-yl)-2,4,5,6-tetrahydro-1H-benz[de] isoquinolin-1-one of formula-II with a hydrogenation catalyst in water;
b) isolating the palonosetron free base.

The '333 and '818 patents disclose use of organic solvents and corrosive acids in hydrogenation of compound of formula II. A growing concern in recent years of international environmental conservation has caused great demands in the chemical industry to reduce the utilization of chemicals that are identified as harmful to and their discharge into the environment. In response to this global concern, once established processes are revisited and, alternative raw materials, reagents and solvents that are environmentally benign including, alternate processes having higher conversion rate, yield and selectivity need to be developed. Under these environmental endeavors, the processes herein described are safer for the environment, for producing a palonosetron free base or its pharmaceutically acceptable salts thereof with the use of water as a solvent in a hydrogenation step.

Hydrogenation is carried out in water in the presence of a suitable hydrogenation catalyst. The hydrogenation catalyst is selected from palladium, platinum, nickel, and rhodium or alumina; preferably, a palladium catalyst, which may be in the form of palladium on carbon or palladium salts such as palladium hydroxide, palladium hydroxide on carbon, and the like; most preferably, the hydrogenation catalyst is palladium on carbon. The palladium content in the catalyst may be about 2.5% to about 35% wt/wt % on carbon, preferably about 10% to about 25% wt/wt % on carbon.

The pressure for hydrogenation can range from about 1 $kg/cm^2$ g to about 20 $kg/cm^2$ g by using hydrogen gas, preferably about 5 $kg/cm^2$ g to about 15 $kg/cm^2$ g, more preferably about 7 $kg/cm^2$ g to about 12 $kg/cm^2$ g. In the presence of water, as a reaction solvent, the reaction proceeds with an addition of about 2 ml to about 30 ml of solvent per gram of compound of formula-II.

The reaction temperature should be sufficient to effect hydrogenation. Typically the reaction temperature may be from about ambient temperature to about reflux temperature. Preferably the reaction temperature is about 45° C. to about 85° C., more preferably at about 60° C. to about 70° C. The hydrogenation process may take from about 5 hours to about 30 hours depending upon the catalyst, pressure and temperature chosen. For instance, a reaction carried out with 20% palladium on carbon and 8 $kg/cm^2$ g to 10 $kg/cm^2$ hydrogen pressure at temperature 65° C. to 70° C., is completed about 25 hours.

The catalyst may be separated or recovered from the reaction mixture by any method known in the art, at the end of the hydrogenation reaction. The resultant water containing the target product may be extracted with an organic solvent under basic conditions by adjusting the pH, wherein the organic solvent may be selected from halogenated solvents such as dichloromethane, dichloroethane, chloroform, carbon tetrachloride and the like, hydrocarbons such as n-hexane, n-heptane, cyclohexane, benzene, toluene and the like; esters such as methyl acetate, ethyl acetate, isopropyl acetate, tertiary butyl acetate and the like; and mixtures thereof. Preferably the organic solvent is selected from dichloromethane, chloroform, toluene, ethyl acetate and a mixture thereof, more preferably the organic solvent is dichloromethane.

The adjustment of pH may be carried out with bases, wherein the bases are known in the art, for example sodium hydroxide, potassium hydroxide and the like, preferably the base is sodium hydroxide. The resultant organic solvent containing palonosetron free base may be concentrated under vacuum to get the residue by any method known in the art, for example distillation, evaporation, rotational drying (such as with the Buchi Rotavapor), freeze-drying, fluidized bed drying, flash drying, spin flash drying, and the like.

The resultant residue may be dissolved in a suitable organic solvent. Suitable organic solvents include, but are not limited to alcohols such as $C_{1-4}$ alcohols selected from methanol, ethanol, isopropanol, n-propanol, butanol, isobutanol and the like; esters such as methyl acetate, ethyl acetate, isopropyl acetate, tertiary butyl acetate and the like; hydrocarbons such as n-hexane, n-heptane, cyclohexane, benzene, toluene and the like; and halogenated solvents such as dichloromethane, dichloroethane, chloroform, carbon tetrachloride and the like; water and their mixtures. Preferably the suitable organic solvent is selected from methanol, ethanol, isopropanol, ethyl acetate, isopropyl acetate, toluene, dichloromethane, water and mixtures thereof; more preferably the suitable organic solvent is methanol, ethanol, isopropanol, ethyl acetate, water and mixtures thereof.

Then, the solution may be heated to dissolve the palonosetron. The temperature suitable for dissolving palonosetron depends on the solvent used and the amount of palonosetron in the solution. Typically, the solution is heated at a temperature of at least about 30° C. to about reflux. Preferably, the solution is heated at about 30° C. to about 85° C., and more preferably at about 40° C. to about 60° C.

The resultant palonosetron free base can be isolated by crystallization, solvent precipitation, concentrated by subjecting the solution to heating, spray drying, freeze drying, evaporation on rotary evaporator under vacuum, agitated thin film evaporator (ATFE) and the like. The palonosetron free base can be recovered by any conventional technique known in the art, for example filtration. Typically, if stirring is involved, the temperature during stirring can range from about −10° C. to about +20° C., preferably at about −10° C. to about +10° C., more preferably at temperature between about 0° C. to about 5° C.

The resultant product may optionally be further dried. Drying can be suitably carried out in a tray dryer, vacuum oven, air oven, fluidized bed drier, spin flash dryer, flash dryer and the like. The drying can be carried out at a temperature ranging from about 30° C. to about 90° C. The drying can be carried out for any desired time until the required product purity is achieved, e.g., a time period ranging from about 1 hour to about 20 hours. A high purity level of the resulting palonosetron free base, obtained by the aforementioned process, may have a chemical purity of at least about 97%, as measured by HPLC, preferably at least about 99%, as measured by HPLC and more preferably at least about 99.5%, as measured by HPLC.

The palonosetron free base recovered using the process of the present invention is in substantially solid amorphous form.

The present invention encompasses methods of preparing isolated palonosetron free base in solid amorphous form and a pharmaceutically acceptable salt thereof with high purity. The processes of the invention allow for economical synthesis, shorter reaction times, and yields of high purity.

The present invention provides pharmaceutically acceptable salts of palonosetron, obtained by a process comprising providing a free base of palonosetron as obtained by the process described above, as a starting material or as an intermediate, where the yield and the purity of the pharmaceutically acceptable salts thereof, preferably hydrochloride salt may have a purity equal to or greater than about 99.8% as determined by HPLC.

The present invention further provides a process for a preparation of a pharmaceutically acceptable salt of palonosetron, preferably palonosetron hydrochloride salt comprising;
  a) providing a palonosetron free base obtained by the process described above dissolved in one or more organic solvents such as $C_{1-4}$ alcohols selected from methanol, ethanol, n-propanol, isopropanol, n-butanol, isobutyl alcohol, tertiary butyl alcohol and the like and mixtures thereof, ethers selected from tetrahydrofuran (THF), dimethylether, diethyl ether, methylethyl ether, diisopropylether, methyltertiarybutyl ether and the like; water and mixtures thereof. Preferably the organic solvents are selected from methanol, ethanol, n-propanol, isopropanol, tetrahydrofuran (THF).
b) heating the solution to dissolve the palonosetron free base. Typically, the solution is heated at a temperature of at least about 30° C. to about reflux. Preferably, the solution is heated at about 30° C. to about 85° C., and more preferably at about 45° C. to about 65° C.
c) treating the resultant solution with hydrochloric acid, where the HCl may be in the form of an aqueous, anhydrous or gas form, for example aqueous hydrochloric acid or solvent containing hydrochloric acid or hydrochloric acid gas, preferably a solvent containing hydrochloric acid can be used.
d) cooling the resultant reaction solution at a temperature from about 20° C. or less. preferably at temperature about 0° C. to about 10° C.; more preferably at temperature between about 0° C. to about 5° C. such that the palonosetron hydrochloride can be isolated by conventional techniques, for example filtration. In the event that stirring is involved, the temperature during stirring can range from about −10° C. to about +20° C., preferably at about −10° C. to about +10° C., more preferably at temperature between about 0° C. to about 5° C.

The resultant product may optionally be further dried. Drying can be suitably carried out in a tray dryer, vacuum oven, air oven, fluidized bed drier, spin flash dryer, flash dryer and the like. The drying can be carried out at a temperature ranging from about 30° C. to about 90° C., preferably at a temperature ranging from about 50° C. to about 70° C., more preferably at about 60° C. to about 70° C. The drying can be carried out for any desired time until the required product purity is achieved, e.g., a time period ranging from about 1 hour to about 20 hours preferably about 10 hours.

The present invention further provides a process for a purification of palonosetron hydrochloride, the process comprising:
a) dissolving the palonosetron hydrochloride, obtained in the above process, in an organic solvent or a mixture with water. The organic solvent includes, but are not limited to $C_{1-4}$ alcohol such as methanol, ethanol, isopropanol, n-propanol, butanol, isobutanol and the like and mixture thereof, esters such as methyl acetate, ethyl acetate, isopropyl acetate, tertiary butyl acetate and the like and mixtures thereof; hydrocarbons such as n-hexane, n-heptane, cyclohexane, benzene, toluene and the like and mixtures thereof. Preferably the organic solvent is selected from methanol, ethanol, isopropanol, ethyl acetate, toluene; and optional mixture with water; more preferably the organic solvent is methanol, ethanol, or isopropanol.
b) heating the solution to dissolve the palonosetron hydrochloride. Typically, the solution is heated at a temperature of at least about 30° C. to about reflux. Preferably, the solution is heated at about 30° C. to about 85° C., and more preferably at about 45° C. to about 65° C.
c) cooling the resultant reaction solution at a temperature from about 20° C. or less, preferably at temperature about 0° C. to about 10° C.; more preferably at temperature between about 0° C. to about 5° C., such that the palonosetron hydrochloride can be isolated by conventional techniques, for example filtration. In the event that stirring is involved, the temperature during stirring can range from about −10° C. to about +20° C., preferably at about −10° C. to about +10° C., more preferably at temperature between about 0° C. to about 5° C.

The resultant product may optionally be further dried. Drying can be suitably carried out in a tray dryer, vacuum oven, air oven, fluidized bed drier, spin flash dryer, flash dryer and the like. The drying can be carried out at a temperature ranging from about 30° C. to about 90° C., preferably at a temperature ranging from about 50° C. to about 70° C., more preferably at about 60° C. to about 70° C. The drying can be carried out for any desired time until the required product purity is achieved, e.g., a time period ranging from about 1 hour to about 20 hours, preferably about 1 hour to about 10 hours.

Optionally the above crystallization process may be repeated one or more times to get a chemical purity typically equal to or greater than about 97%, preferably equal to or greater than about 99%, more preferably equal to or greater than about 99.8%, by weight as determined using HPLC.

The present invention provides a palonosetron hydrochloride, obtained by the process described herein, having a chemical purity of at least about 97%, as measured by HPLC, preferably at least about 99% as measured by HPLC, and more preferably at least about 99.8%, as measured by HPLC; a diastereomeric purity of at least about 99.5%, as measured by HPLC, preferably at least about 99.8%, as measured by HPLC; and substantially free of 2-(1-azabicyclo[2.2.2]oct-3-yl)-2,4,5,6-tetrahydro-1H-benz[de]isoquinolin-1-one of formula-II (unreacted impurity), (II)

wherein the word "substantially free" refers to palonosetron hydrochloride having less than about 0.1%, of formula-II, as measured by HPLC, more preferably less than about 0.05% of formula-II, as measured by HPLC.

The '333 patent discloses palonosetron free base which was isolated as a semisolid by evaporation of a reaction solvent. In contrast, the process herein described arrives at a palonosetron free base, which may be isolated as a solid by a crystallization process and contains substantially low content of unreacted formula II. Particularly, the process herein described allows that a palonosetron free base may be isolated as a solid, particularly in an amorphous form that remains solid at room temperature.

The '283 publication discloses palonosetron free base to be isolated in Example 11. However, the '283 patent uses the same synthesis route as the '333 patent to prepare the palonosetron and/or its salts. The '283 patent arrives at the levels of purity disclosed therein by subjecting the palonosetron salts to purification via multiple re-crystallization steps, from which the free base isolated. In contrast, the process herein described arrives at a palonosetron free base, which may be isolated as a solid by a crystallization process and contains substantially low content of unreacted formula-II, via a different route of synthesis. Said synthesis entails hydrogenation of formula-II in the presence of water.

A comparative preparation of palonosetron using a hydrogenation process in the presence of acetic acid and perchloric acid or in an ethanol and water mixture as disclosed in other processes for, yielded a palonosetron hydrochloride, that had lower purity levels than the present process. Further, these processes yielded a final product that contained substantial amounts of residual 2-(1-azabicyclo[2.2.2]oct-3-yl)-2,4,5,6-tetrahydro-1H-benz[de]isoquinolin-1-one of formula-II (herein referred to as "unreacted impurity") even after repeated purifications. These results are summarized in Table-I and Table-II, as shown below under Examples 5 and 6 where values are reported as weight percent (w/w %) as determined by HPLC.

The present invention further provides palonosetron free base or a pharmaceutically acceptable salt, obtained by the processes described herein, having relatively low content of one or more organic volatile impurities.

The present invention provides a palonosetron free base or a pharmaceutically acceptable salt thereof; preferably the hydrochloride salt obtained using the process of the described herein, may have a residual solvent content that is within the limits given by the International Conference on Harmonization of Technical Requirements for Registration of Pharmaceuticals for Human Use ("ICH") guidelines. The guideline solvent level depends on the type of solvent but is not more than about 5000 ppm, or about 4000 ppm, or about 3000 ppm.

The present invention provides a palonosetron hydrochloride, obtained by the process disclosed herein, having less than about 800 parts per million (ppm) $C_{1-4}$ alcohols such as methanol, ethanol, isopropanol, preferably less than about 200 ppm; less than about 500 ppm ethyl acetate, preferably less than about 100 ppm; less than about 500 ppm toluene, preferably less than about 100 ppm; less than about 500 ppm cyclohexane, preferably less than about 200 ppm; less than about 500 ppm tetrahydrofuran, preferably less than about 100 ppm; less than about 500 ppm acetic acid, preferably less than about 100 ppm; less than about 250 ppm petroleum ether, preferably less than about 100 ppm; less than about 500 ppm dichloromethane, preferably less than about 100 ppm; less than about 500 ppm n-hexane, preferably less than about 100 ppm; less than about 500 ppm dimethyl formamide, preferably less than about 100 ppm; less than about 200 ppm triethyl amine, preferably less than about 10 ppm. The present invention further provides palonosetron hydrochloride, obtained by the process disclosed herein, having less than about 6 ppm acetone; less than about 9 ppm methanol; less than about 8 ppm ethanol; less than about 3 ppm isopropanol; less than about 3 ppm ethyl acetate; less than about 3 ppm hexane; less than 3 ppm toluene; less than about 6 ppm dichloromethane; less than about 1 ppm tetrahydrofuran and less than about 7 ppm dimethyl formamide.

The present invention provides palonosetron free base in crystalline form-G.

The present invention also provides for the preparation of palonosetron free base of form-G in crystalline form and a pharmaceutically acceptable salt thereof.

The present invention provides characterization via X-ray powder diffraction pattern and/or melting point of a palonosetron free base in an amorphous form and a crystalline form-G. The X-Ray powder diffraction can be measured by an X-ray powder Diffractometer equipped with a Cu-anode ($\lambda$=1.54 Angstrom), X-ray source operated at 45 kV, 40 mA and a Ni filter is used to strip K-beta radiation. Two-theta calibration is performed using an NIST SRM 640c Si standard. The sample was analyzed using the following instrument parameters: measuring range=2-50° 2θ; step width=0.017°; and measuring time per step=5 sec.

The present invention further provides a palonosetron free base in crystalline form-G, with a differential scanning calorimetric thermogram, which is as substantially shown in FIG. 5, as measured by a Differential Scanning Calorimeter (DSC 822, Mettler Toledo) at a scan rate of 10° C. per minute with an Indium standard. Palonosetron free base in crystalline form-G exhibits a predominant endotherm peak at about 95.71° C. Whereupon, the endotherm measured by a particular differential scanning calorimeter is dependent upon a number of factors, including the rate of heating (i.e., scan rate), the calibration standard utilized, instrument calibration, relative humidity, and upon the chemical purity of the sample being tested. Thus, an endotherm as measured by DSC on the instrument identified above may vary by as much as ±1° C. or even ±2° C.

Figure 6:
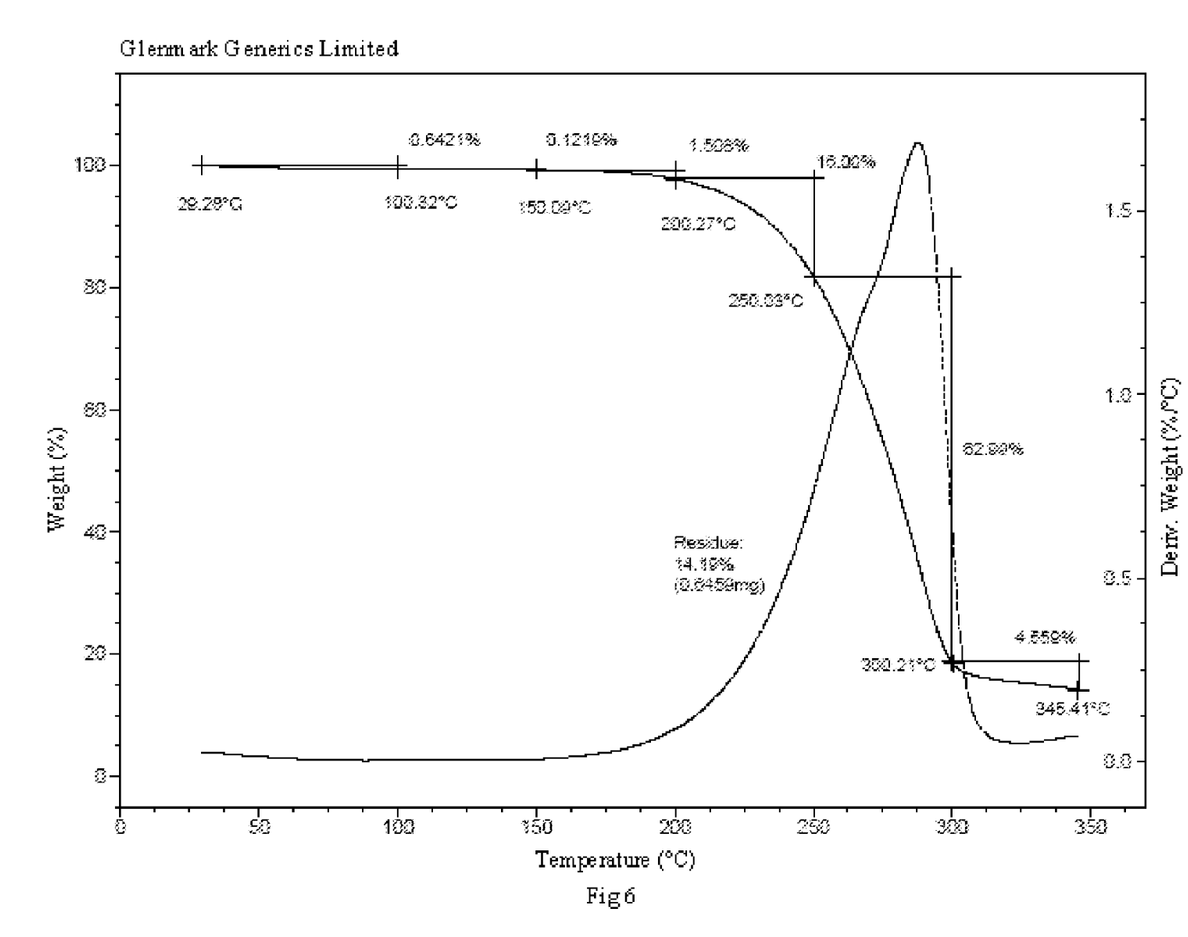
FIG. 6 is a characteristic thermogravimetric analysis (TGA) of palonosetron free base in crystalline form-G.

The present invention further provides a palonosetron free base in crystalline form-G, with a thermogravimetric analysis (TGA), which is as substantially shown in FIG. 6, recorded on TGA Q500 V 20.6 in platinum pan with temp rise 10° C./min in the range 30° C. to 350° C.

The present invention further provides a process for the preparation of palonosetron free base in crystalline form-G, comprising
a) providing a solution of palonosetron hydrochloride, obtained by the processes herein described above, in a water immiscible organic solvent and water;
b) treating with a base;
c) concentrating the water immiscible organic solvent; and
d) crystallizing the resultant residue in a suitable organic solvent.

Any form of a palonosetron or a pharmaceutically acceptable salt thereof, preferably hydrochloride salt, can be used as a starting material in the process of making the palonosetron free base in crystalline form-G of the present invention.

Ideally, palonosetron hydrochloride, obtained by the processes herein described previously, is the starting material in the process of making the palonosetron free base in crystalline form-G.

Useful water immiscible organic solvent for carrying out the process of the present invention include, but are not limited to $C_4$ to $C_7$ ketones such as methyl ethyl ketone, methyl isobutyl ketone, cyclohexanone and the like and mixtures thereof; esters such as methyl acetate, ethyl acetate, isopropyl acetate, tertiary butyl acetate and the like and mixtures thereof; halogenated solvents such as dichloromethane, dichloroethane, chloroform, carbon tetrachloride and the like and mixtures thereof; ethers such as dimethylether, diethyl ether, methylethylether, diisopropylether, methyltertiarybutyl ether and the like and mixtures thereof; hydrocarbon solvents such as n-hexane, n-heptane, cyclohexane, benzene, toluene and the like and mixtures thereof. Preferably the water immiscible organic solvent is selected from dichloromethane, chloroform, toluene, ethyl acetate, methylethylether, and a mixture thereof, more preferably the organic solvent selected from dichloromethane, toluene, or ethyl acetate; most preferably dichloromethane can be used as water immiscible organic solvent.

The suitable bases includes an alkali or an alkaline earth metal such as sodium hydroxide, potassium hydroxide, barium hydroxide, potassium t-butoxide, sodium carbonate, potassium carbonate and the like and mixtures thereof. Preferably the base is sodium hydroxide, or potassium hydroxide. The source of base can be added either as solution in water or it may be added as solid to the solution of palonosetron, its pharmaceutically acceptable salts in an organic solvent. The sequence of addition of water and/or base is not a criteria which needs monitoring, either can be added first.

The separation of the aqueous and organic layers can be carried out by employing any conventional technique known in the art and the solvent can also be removed from the solution using techniques known in the art including, for example, distillation, evaporation, rotational drying (such as with the Buchi Rotavapor), freeze-drying, fluidized bed drying, flash drying, spin flash drying, and the like.

The resultant residue may be dissolved in a suitable organic solvent. which includes, but are not limited to alcohols such as $C_{1-4}$ alcohols such as methanol, ethanol, isopropanol, n-propanol, butanol, isobutanol and the like, esters such as methyl acetate, ethyl acetate, isopropyl acetate, tertiary butyl acetate and the like; hydrocarbons such as n-hexane, n-heptane, cyclohexane, benzene, toluene and the like, and halogenated solvents such as dichloromethane, ethylene dichloride, chloroform, carbon tetrachloride and the like; water and their mixtures. Preferably the suitable organic solvent is selected from methanol, ethanol, isopropanol, ethyl acetate, isopropyl acetate, toluene, dichloromethane, water and mixtures thereof; more preferably the suitable organic solvent is methanol, ethanol, isopropanol, ethyl acetate, water and mixtures thereof.

The solution may be heated to dissolve the palonosetron free base. The temperature suitable for dissolving palonosetron free base depends on the solvent used and the amount of palonosetron free base in the solution. Typically, the solution is heated at a temperature of at least about 30° C. to about reflux. Preferably, the solution is heated at about 30° C. to about 85° C., and more preferably at about 40° C. to about 60° C. The resultant reaction solution may be cooled at a temperature from about 20° C. or less such that the palonosetron free base can be isolated by conventional techniques, for example filtration. In the event that stirring is involved, the temperature during stirring can range from about −10° C. to about +20° C., preferably at about −10 to about +10° C., more preferably at temperature between 0° C. to 5° C.

The resultant product may optionally be further dried. Drying can be suitably carried out in a tray dryer, vacuum oven, air oven, fluidized bed drier, spin flash dryer, flash dryer and the like. The drying can be carried out at a temperature from about 30° C. to about 90° C., preferably from about 50° C. to about 70° C., more preferably from about 60° C. to about 70° C. The drying can be carried out for any desired time until the required product purity is achieved, e.g., a time period ranging from about 1 hour to about 20 hours, preferably from about 1 hour to about 10 hours.

The present invention provides a process for the conversion of a palonosetron free base in crystalline form-G into palonosetron hydrochloride salt; comprising:

a) providing a palonosetron free base in crystalline form-G, obtained by the process described above, dissolved in one or more organic solvents such as $C_{1-4}$ alcohols selected from methanol, ethanol, n-propanol, isopropanol, n-butanol, isobutyl alcohol, tertiary butyl alcohol and the like and mixtures thereof, ethers selected from tetrahydrofuran (THF), dimethylether, diethyl ether, methylethylether, diisopropylether, methyltertiarybutyl ether and the like; water and mixtures thereof. Preferably the organic solvents are selected from methanol, ethanol, n-propanol, isopropanol, tetrahydrofuran (THF).

b) heating the solution to dissolve the palonosetron free base. Typically, the solution is heated at a temperature of at least about 30° C. to about reflux. Preferably, the solution is heated at about 30° C. to about 85° C., and more preferably at about 45° C. to about 65° C.

c) treating the resultant solution with hydrochloric acid, where the HCl may be in the form of an aqueous, anhydrous or gas form, for example aqueous hydrochloric acid or solvent containing hydrochloric acid or hydrochloric acid gas, preferably a solvent containing hydrochloric acid can be used.

d) cooling the resultant reaction solution at a temperature from about 20° C. or less. preferably at temperature about 0° C. to about 10° C.; more preferably at temperature between about 0° C. to about 5° C. such that the palonosetron hydrochloride can be isolated by conventional techniques, for example filtration. In the event that stirring is involved, the temperature during stirring can range from about −10° C. to about +20° C., preferably at about −10° C. to about +10° C., more preferably at temperature between about 0° C. to about 5° C.

The resultant product may optionally be further dried. Drying can be suitably carried out in a tray dryer, vacuum oven, air oven, fluidized bed drier, spin flash dryer, flash dryer and the like. The drying can be carried out at a temperature ranging from about 30° C. to about 90° C., preferably at a temperature ranging from about 50° C. to about 70° C., more preferably at about 60° C. to about 70° C. The drying can be carried out for any desired time until the required product purity is achieved, e.g., a time period ranging from about 1 hour to about 20 hours, preferably from about 1 hour to about 10 hours.

The present invention provides a preparation of other pharmaceutically acceptable salts of palonosetron, the process comprising reacting either a palonosetron free base in a solid amorphous form or a crystalline form-G as starting material or as an intermediate, with pharmaceutically acceptable salts. The pharmaceutical acceptable salts include acid addition salts formed with inorganic acids or with organic acids. The inorganic acids may be selected from hydrochloric acid, hydrobromic acid, hydroiodic acid, sulfuric acid, nitric acid, phosphoric acid, and the like; organic acids such as acetic acid, propionic acid, hexanoic acid, heptanoic acid, malonic acid, succinic acid, malic acid, malice acid, tartaric acid, citric acid, oxalic acid, and the like, preferably hydrochloric acid.

The present invention provides a palonosetron hydrochloride, obtained by the above process, as analyzed using high performance liquid chromatography ("HPLC") with the conditions described below:

| Column and Packing: | Inertsil $C_8$-3, 150 × 4.6 mm, 5µ | |
|---|---|---|
| Column temperature: | 40° C. | |
| Mobile Phase: Buffer: | Add 1 mL of Triethylamine in 1000 mL of water. Adjust pH to 7.0 with o-phosphoric acid. | |
| Time (min.) | % Buffer | % Acetonitrile |
| 0.01 | 85 | 15 |
| 30 | 50 | 50 |
| 40 | 50 | 50 |
| 42 | 85 | 15 |
| 50 | 85 | 15 |
| Diluent: | Buffer:Acetonitrile (50:50, v/v) | |
| Flow Rate: | 1.0 mL/minut | |
| Detection: | UV 210 nm | |
| Injection Volume: | 10 µL | |

The present invention provides palonosetron hydrochloride, obtained by the above process, as analyzed using Gas chromatography ("GC") for measuring the residual solvents amount by the conditions described below:
Method-I

| | |
|---|---|
| Instrument | Gas chromatograph equipped with FID detector and Headspace (Combi Pal) |
| Column | DB-WAX, 60 m × 0.32 mm, 0.5 μm |
| Column Temp. | 40° C. (hold for 27 minutes) to 120° C. @ 20° C./minute (hold at 120° C. for 2 minutes) to 240° C. @ 60° C./minute (hold at 240° C. for 10 minutes) |
| Injector/detector | 250° C./300° C. |
| Carrier gas | Nitrogen @ 15 cm/sec., linear velocity |
| Pressure ramp | 7.7 psi (hold for 30 minutes) to 25 psi @ 5 psi/minute (hold at 25 psi for 12 minutes) |
| Split Ratio | (10:1) |

Head Space Parameters:

| | |
|---|---|
| Incubation Temperature | 95° C. |
| Incubation Time | 15 minutes |
| Agitation Speed | 600 rpm |
| Syringe Temperature | 115° C. |
| Injection Volume | 1 ml |

Sample Preparation

The sample is dissolved in Dimethyl sulfoxide about 400 mg in 5 ml.
Method-II

| | |
|---|---|
| Instrument | Gas chromatograph equipped with FID detector and autosampler. |
| Column | DB-WAX, 30 m × 0.53 mmID, 1.0 μm |
| Column Temp. | 50° C. (hold for 5 minutes) to 220° C. @ 20° C./minute (hold at 220° C. for 10 minutes) |
| Injector/detector | 250° C./300° C. |
| Carrier gas | Nitrogen @ 26 cm/sec., linear velocity |
| Split Ratio | (2:1) |
| Injection Volume | 1 μL |

Sample Preparation

The sample is dissolved in methanol about 500 mg in 10 ml.

Method-I is provided for analyzing the residual solvents described in [0070] except dimethyl formamide, wherein the Method-II is provided.

The present invention also encompasses a pharmaceutical composition comprising either an isolated palonosetron free base in solid amorphous form and a pharmaceutically acceptable salt thereof or a palonosetron free base of form-G in crystalline form and a pharmaceutically acceptable salt thereof.

The present invention provides for a pharmaceutical composition comprising the novel amorphous free base of palonosetron and the crystalline free base form-G of palonosetron, obtained by the processes herein described above, and the use of said pharmaceutical composition as an antiemetic and anti-nauseant agent.

The present invention further provides an isolated palonosetron free base obtained by processes described herein, which is stable and is well suited for use in preparing pharmaceutical formulations. The pharmaceutical formulations according to the present invention can be administered by any appropriate route, for example orally, parenterally, or intravenously, in liquids or solid form.

As used herein, the term "isolated" refers to a chemical state well known among pharmaceutical chemists wherein the recited pharmaceutical ingredient has been separated from the medium in which it was created into a relatively pure physical state, before it is mixed with other pharmaceutical ingredients.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

Pharmaceutically acceptable salts include acid addition salts formed with inorganic acids or with organic acids. Inorganic acids such as hydrochloric acid, hydrobromic acid, hydroiodic acid, sulfuric acid, nitric acid, phosphoric acid, and the like; organic acids such as acetic acid, propionic acid, hexanoic acid, heptanoic acid, malonic acid, succinic acid, malic acid, malice acid, tartaric acid, citric acid, oxalic acid, and the like.

As used herein, the term "solid" refers to a chemical substance having a definite shape and volume; one that is neither liquid nor gaseous, before it is mixed with other pharmaceutical ingredients.

The present invention further provides a palonosetron free base, as disclosed herein for use in a pharmaceutical composition, previously described, which may independently have a $D_{50}$ and $D_{90}$ particle size less than about 300 microns, preferably less than about 200 microns, more preferably less than about 150 microns, still more preferably less than about 50 microns and most preferably less than about 10 microns. Whereupon, the notation $D_x$ means that X % of particles have a diameter less than a specified diameter D. Thus, a $D_{50}$ of about 300 microns means that 50% of the micronized particles in a composition have a diameter less than about 300 microns. Any milling, grinding, micronizing or other particle size reduction method known in the art can be used to bring the solid state palonosetron free base into any desired particle size range set forth above.

Preferred modes of administrations of the pharmaceutical compositions comprising the active compound may be injectable or oral. The pharmaceutical compositions, so described, will generally include an inert diluent or an edible carrier. They may be enclosed in gelatin capsules (for oral use) or compressed into tablets (for oral or buccal use) or formulated into troches (for buccal use). For these purposes, the active compound can be incorporated with excipients and used in the form of tablets, troches, or capsules. Pharmaceutically compatible binding agents, and/or adjuvant materials can be included as part of the composition.

Tablets, pills, capsules, troches and the like may suitably contain any of the following ingredients, or compounds of a similar nature, which are pharmaceutically acceptable: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The pharmaceutical composition may be administered as a component of an elixir, suspension, syrup, wafer, orally disintegrating film, orally disintegrating tablet, chewing gum or the like. A syrup may contain, in addition to the active compounds, sucrose as a sweetening agent and certain preservatives, dyes and colorings and flavors.

The pharmaceutical composition may be in the form of solutions or suspensions used for injection, which may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride, mannitol and dextrose. An injectable preparation can be enclosed in ampoules, disposable syringes or multiple dose vials made of glass or plastic.

The following examples are provided to enable one skilled in the art to practice the invention and are merely illustrative of the invention. The examples should not be read as limiting the scope of the invention as defined in the features and advantages.

EXAMPLES

Example 1

The preparation of palonosetron free base from 2-(1-azabicyclo[2.2.2]oct-3-yl)-2,4,5,6-tetrahydro-1H-benz[de]isoquinolin-1-one of formula-II.

This reaction is generally shown below in Scheme 1.

Into an autoclave: water (400 ml) and 2-(1-azabicyclo[2.2.2]oct-3-yl)-2,4,5,6-tetrahydro-1H-benz[de]isoquinolin-1-one (50 gm) were charged. Then charged 20% palladium carbon (5 gm) at 25° C.-30° C. and heated the reaction mass at 65-70° C. Passed hydrogen gas upto 8 kg at 65° C.-70° C. and maintained for 25 hours. Filtered the reaction mass through hyflo bed at 25° C.-30° C. and adjusted the pH to 12 with aqueous sodium hydroxide (20 gm) dissolved in water (40 ml). Extracted the reaction product with dichloromethane (1×250 ml and 2×125 ml) and washed with water (2×125 ml) and dichloromethane was removed by distillation from the reaction mass under vacuum at 30° C.-35° C. The resulting residue was dissolved in ethyl acetate (35 ml) and methanol (70 ml) at 25° C.-30° C. and added water (525 ml) at 25° C. to 30° C. Cooled the solution to 0° C.-5° C. and stirred for 2 hours. The resulting solid was filtered and washed with purified water (50 ml). The wet product was dried at 40° C.-45° C. under reduced pressure to provide the crude palonosetron free base Yield: 21.0 g Mass m/z 297.40

HPLC: diastereomeric purity: S-isomer: 55.10%, R-isomer: 44.89%, HPLC chemical

Purity: 99.49%. Unreacted impurity: 0.27%

The XRD is set forth in FIG. 1.

The DSC is set forth in FIG. 2.

Figure 3:
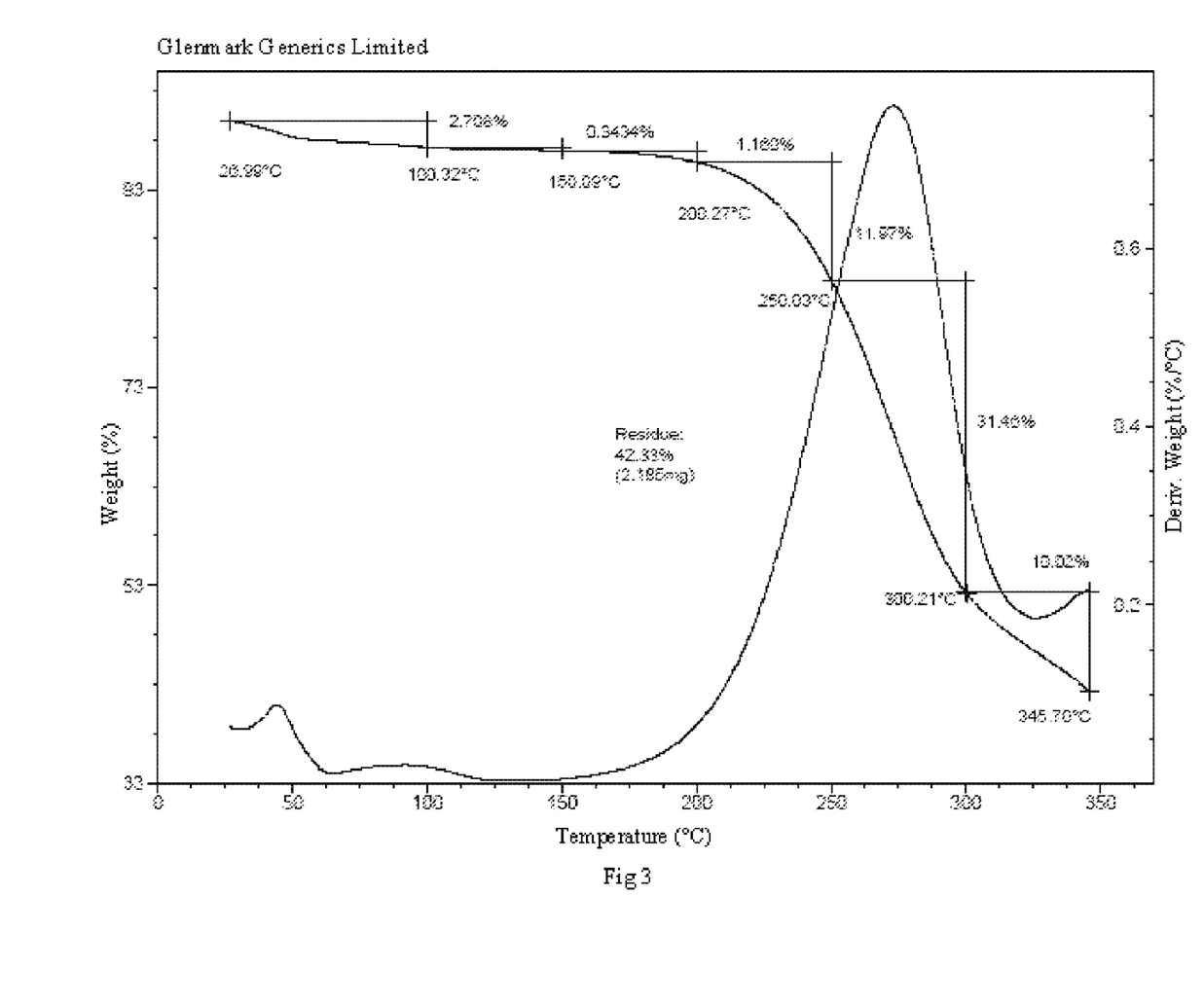
FIG. 3 is a characteristic thermogravimetric analysis (TGA) of palonosetron free base in an amorphous form.

The TGA is set forth in FIG. 3.

Example 2

The preparation of palonosetron hydrochloride from palonosetron free base.

Charged ethanol (100 ml) and palonosetron free base (20 g, obtained from ex-1) in a round bottom flask. Heated the reaction mass at temperature 60° C.-65° C. and charged 20% Isopropanolic hydrochloride (40 ml). Stirred the reaction mass at temperature 60-65° C. for 30 minutes. Cooled to 25° C.-30° C. and stirred for 2 hours. The resulting solid was filtered and washed with ethanol (10 ml). The wet product was dried at 60° C.-65° C. under reduced pressure to provide the palonosetron hydrochloride (21 g).

HPLC: diastereomeric purity: S-isomer: 95.19%, R-isomer: 4.80%

HPLC chemical purity: 99.85%

Unreacted impurity: 0.11%

Example 3

Purification of palonosetron hydrochloride.

Palonosetron hydrochloride (20 g, obtained from ex-2) was dissolved in methanol (30 ml) at temperature 60° C.-65° C. Stirred the reaction mass at 60° C.-65° C. for 30 minutes. Cooled to 10° C.-15° C. and stirred for 60 minutes. The resulting solid was filtered and washed with methanol (10 ml). The wet product was dried at 55° C.-60° C. under reduced pressure to provide the palonosetron hydrochloride (17 g).

HPLC: diastereomeric purity: S-isomer: 99.88%, R-isomer: 0.11%

HPLC chemical purity: 99.97%. Unreacted impurity: 0.02%

Figure 7:
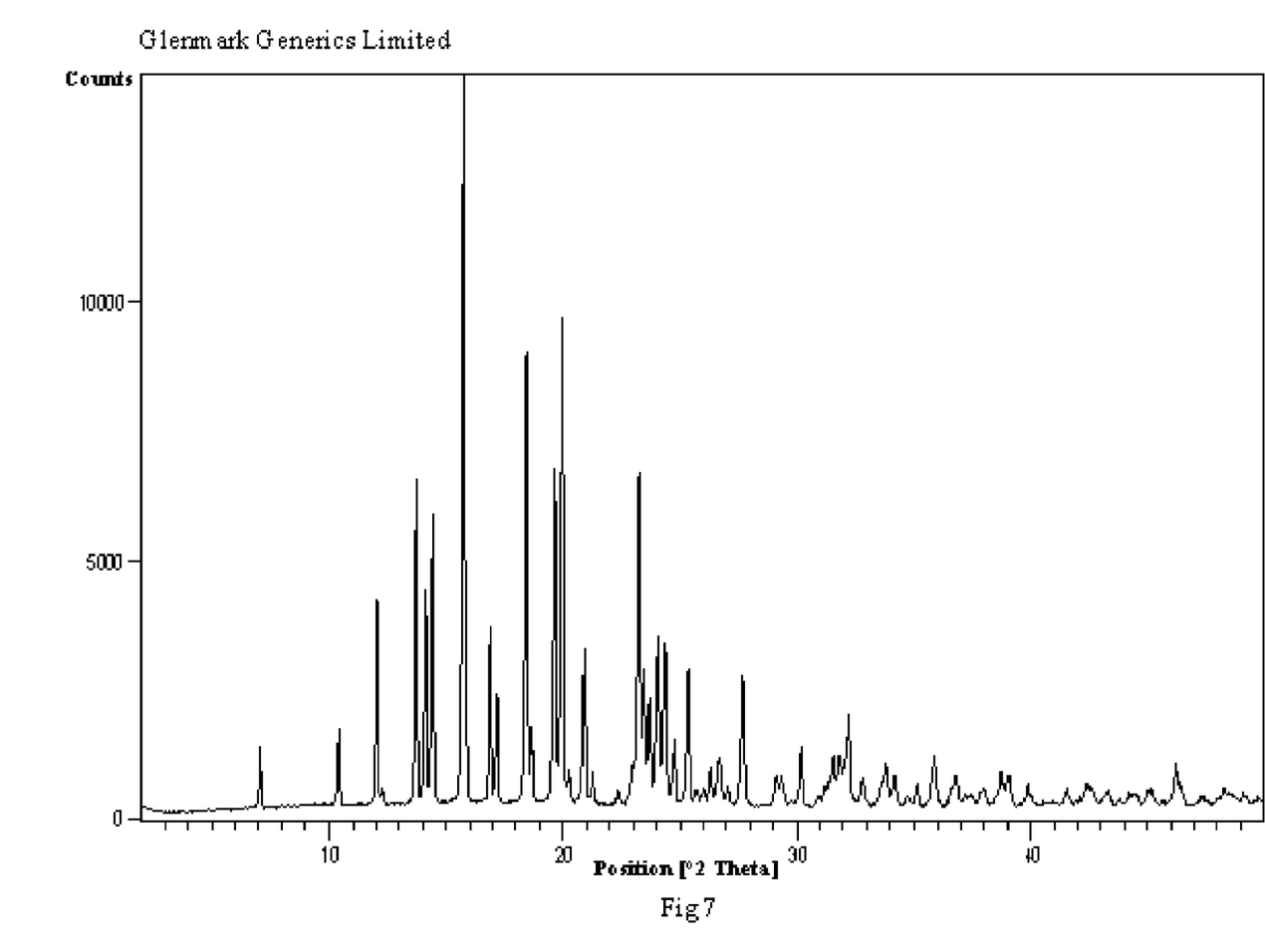
FIG. 7 is a characteristic XRPD of palonosetron hydrochloride as obtained in Example-3

The XRD is set forth in FIG. 7.

Figure 8:
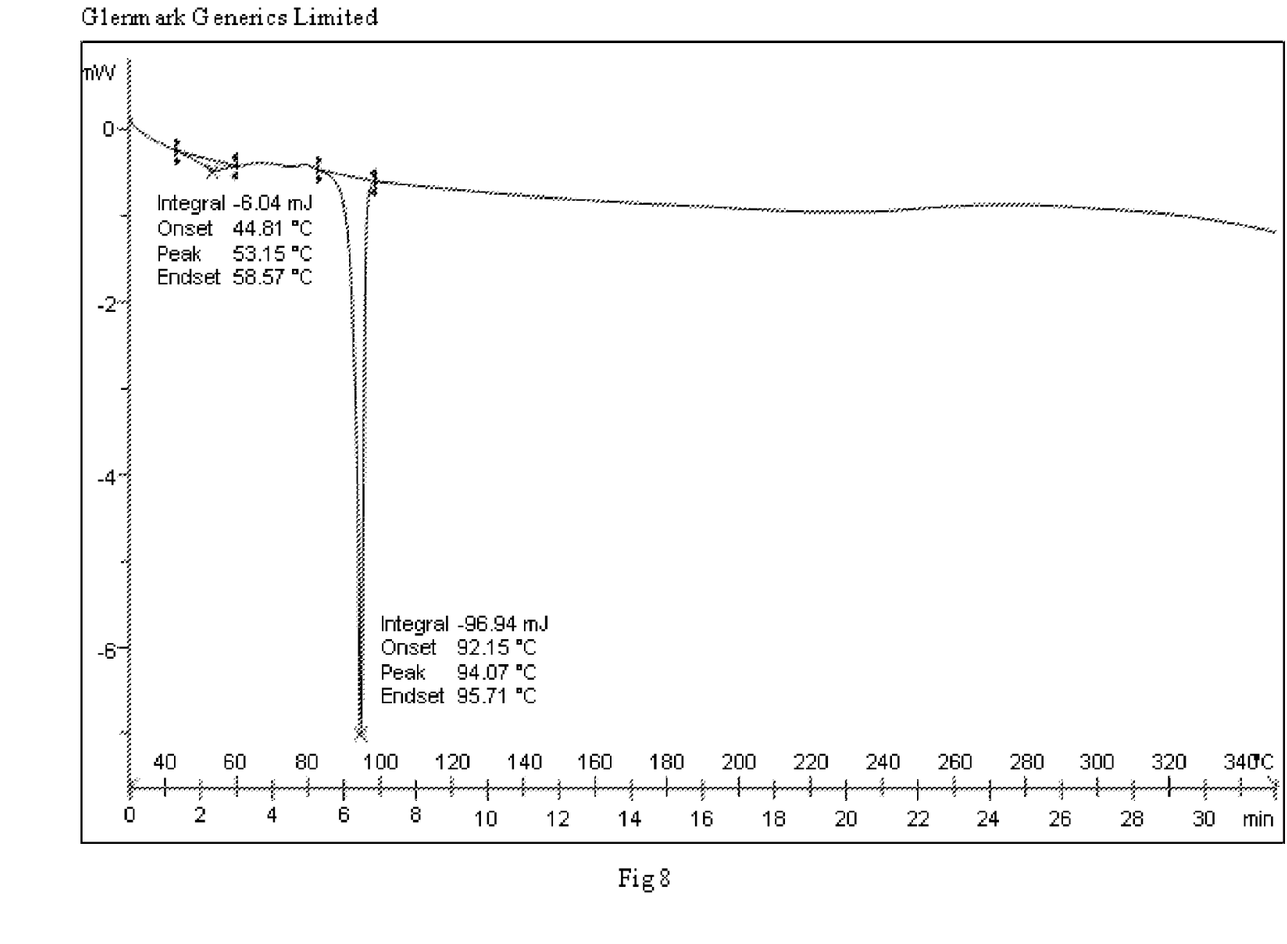
FIG. 8 is a characteristic DSC thermogram of palonosetron hydrochloride as obtained in Example-3

The DSC is set forth in FIG. 8.

Figure 9:
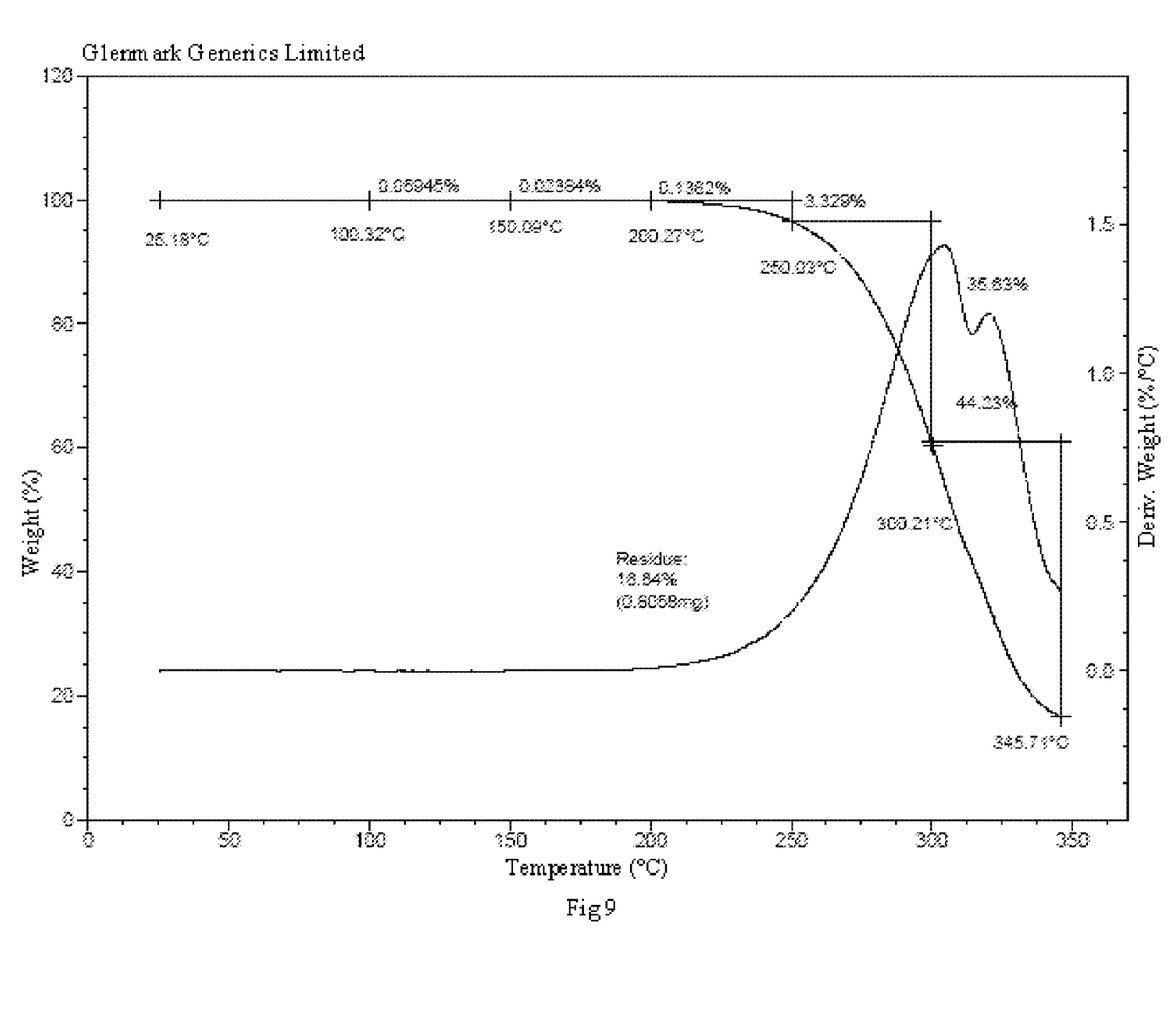
FIG. 9 is a characteristic thermogravimetric analysis (TGA) of palonosetron hydrochloride as obtained in Example-3

The TGA is set forth in FIG. 9.

Residual Solvents:

| Solvent | Content (in ppm) | Solvent | Content (in ppm) |
| --- | --- | --- | --- |
| Acetone | below 6 | Hexane | below 3 |
| Methanol | below 9 | Toluene | below 3 |
| Ethanol | below 8 | Dichloromethane | below 6 |
| Isopropanol | below 3 | Tetrahydrofuran | below 1 |
| Ethyl acetate | below 3 | Dimethylformamide | below 7 |

Example 4

The preparation of palonosetron free base in crystalline form-G.

Palonosetron hydrochloride (50 g) was dissolved in dichloromethane (250 ml) and water (250 ml) followed by addition of aqueous sodium hydroxide (2 g) dissolved in water (20 ml) then adjusted to pH 10. The reaction mass was stirred for 15 minutes at 25° C.-30° C. Separated the dichloromethane layer and washed with water (2×125 ml) and dichloromethane was removed by distillation from the reaction mass under vacuum at 30° C.-35° C. The resulting residue was dissolved in ethyl acetate (20 ml) and methanol (40 ml) at 25° C.-30° C. and added water (300 ml) at 25° C.-30° C. Cooled the solution to 0° C.-5° C. and stirred for 2 hours. The resulting solid was filtered and washed with purified water (20 ml). The wet product was dried at 40° C.-45° C. under reduced pressure to provide the palonosetron free base (13.0 g).

HPLC: diastereomeric purity: S-isomer: 99.94%, R-isomer: 0.05%

HPLC chemical purity: 99.89%

The XRD is set forth in FIG. 4.

The DSC is set forth in FIG. 5.

The TGA is set forth in FIG. 6.

Example 5

Palonosetron hydrochloride was prepared from 2-(1-azabicyclo[2.2.2]oct-3-yl)-2,4,5,6-tetrahydro-1H-benz[de]isoquinolin-1-one of formula-H using acetic acid and perchloric acid as reaction solvent Charged acetic acid (1562.5 ml), 70% perchloric acid solution (50 ml) and 2-(1-azabicyclo[2.2.2]oct-3-yl)-2,4,5,6-tetrahydro-1H-benz[de]isoquinolin-1-one (100 gm) in an autoclave. Charged 20% palladium hydroxide (31.25 gm) at 25° C.-30° C. and heated the reaction mass at 85° C. Passed hydrogen gas up to 50 psi at 85° C. and maintained for 28 hours. Filtered the reaction mass through hyflo bed at 25° C.-30° C. and washed the hyflo bed with water (100 ml). The filtrate was concentrated under vacuum by distillation of water and the resulting residue was dissolved in water and basified to pH 10 with ammonium hydroxide solution (200 ml). Extracted with ethyl acetate and the ethyl acetate layer was dried over anhydrous potassium carbonate, filtered, and evaporated to give a semi solid mass. The resulting semisolid was dissolved in ethanol and added ethanolic hydrochloric acid at 25° C.-30° C. Filtered and washed with ethanol (50 ml). The wet product was dried at 60° C.-65° C. under reduced pressure to provide the crude palonosetron hydrochloride (56.25 g). The crude palonosetron hydrochloride was further purified in ethanol for four times to gave the pure palonosetron hydrochloride.

Below are measurements using HPLC of three batches of palonosetron hydrochloride prepared as in Example-5, with the solvents used in the '333 patent in a process for the preparation of palonosetron hydrochloride. The numerical values (% wgt/wgt) set forth below in Table I summarize purity levels of the palonosetron hydrochloride. The left column shows the purity levels of palonosetron hydrochloride (crude), batches 1 to 3 obtained using the solvents of the '333 patent. The right column shows the ensuing levels of purity of said batches, after having been purified in ethanol.

TABLE I

| Batch | Palonosetron hydrochloride (crude) | Pure Palonosetron hydrochloride (after four purifications) |
|---|---|---|
| 1 | S-isomer: 78.27% | S-isomer: 97.63% |
|   | R-isomer: 16.41% | R-isomer: 1.59% |
|   | Unreacted impurity: 0.33% | Unreacted impurity: 0.28% |
| 2 | S-isomer: 87.96% | S-isomer: 98.19% |
|   | R-isomer: 8.17% | R-isomer: 1.13% |
|   | Unreacted impurity: 0.47% | Unreacted impurity: 0.34% |
| 3 | S-isomer: 84.80% | S-isomer: 96.53% |
|   | R-isomer: 12.43% | R-isomer: 2.10% |
|   | Unreacted impurity: 1.34% | Unreacted impurity: 0.89% |

Example 6

Process for the preparation of palonosetron hydrochloride from 2-(1-azabicyclo[2.2.2]oct-3-yl)-2,4,5,6-tetrahydro-1H-benz[de]isoquinolin-1-one of formula-II using ethanol and water as reaction solvent. (following the '818 patent) ethanol (160 ml), water (640 ml) and 2-(1-azabicyclo[2.2.2]oct-3-yl)-2,4,5,6-tetrahydro-1H-benz[Charged de]isoquinolin-1-one (100 gm) in an autoclave. Charged 20% palladium carbon (10 gm) at 25-30° C. and heated the reaction mass at 70° C. Passed hydrogen gas up to 8 kg at 70° C. and maintained for 48 hours. Filtered the reaction mass through hyflo bed at 25° C.-30° C. and washed the hyflo bed with water (100 ml). Adjusted the pH to 12 with aqueous sodium hydroxide (40 gm of sodium hydroxide dissolved in 80 ml of water). Extracted the reaction product with dichloromethane (1×500 ml and 2×250 ml) and washed with water (2×500 ml), dried the dichloromethane layer with sodium sulphate (50 gm) and dichloromethane was removed by distillation from the reaction mass under vacuum at 30° C.-35° C. The resulting residue was dissolved in ethanol (250 ml) and heated to 65° C. Charged 20% Isopropanolic hydrochloric acid (160 ml) at 65° C., cooled the solution to 25° C.-30° C. and stirred the reaction for 2 hours. The resulting solid was filtered and washed with ethanol (2×50 ml). The wet product was dried at 60° C. to 65° C. under reduced pressure to provide the crude palonosetron hydrochloride (42.0 g). The crude palonosetron hydrochloride was further purified in ethanol for three times to obtain pure palonosetron hydrochloride.

Below are measurements using HPLC of three batches of palonosetron hydrochloride prepared, with the solvents used in the '818 patent in a process for the preparation of palonosetron hydrochloride. The numerical values (% wgt/wgt) set forth below in Table II summarize purity levels of the palonosetron hydrochloride. The left column shows the purity levels of palonosetron hydrochloride (crude), batches 1 to 3 obtained using the solvents of the '818 patent. The right column shows the ensuing levels of purity of said batches, after having been purified in ethanol.

TABLE II

| Batch | Palonosetron hydrochloride (crude) | Pure Palonosetron hydrochloride (after Three purifications) |
|---|---|---|
| 1 | S-isomer: 88.42% | S-isomer: 97.29% |
|   | R-isomer: 10.47% | R-isomer: 1.80% |
|   | Unreacted impurity: 0.38% | Unreacted impurity: 0.44% |
| 2 | S-isomer: 74.47% | S-isomer: 96.78% |
|   | R-isomer: 22.55% | R-isomer: 2.04% |
|   | Unreacted impurity: 1.18% | Unreacted impurity: 0.96% |
| 3 | S-isomer: 89.17% | S-isomer: 97.75% |
|   | R-isomer: 9.58% | R-isomer: 1.73% |
|   | Unreacted impurity: 0.40% | Unreacted impurity: 0.33% |

Tables I and II show that levels of purity of palonosetron hydrochloride obtained from palonosetron free base, which use solvents, other than water alone, in contrast to the process described herein, are lower than levels of purity of palonosetron hydrochloride obtained from palonosetron free base, either from an isolated solid amorphous form or crystalline form-G, as obtained processes described herein.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. Isolated palonosetron free base in solid crystalline form-G, having an X-ray diffraction pattern in accordance with FIG. 4, and a differential scanning calorimetric thermogram, with a predominant endotherm peak at about 95.71° C., in accordance with FIG. 5.

2. A process for the preparation of palonosetron free base in solid crystalline form-G of claim 1 comprising
    a) hydrogenating the 2-(1-azabicyclo[2.2.2]oct-3-yl)-2,4,5,6-tetrahydro-1H-benz[de]isoquinolin-1-one of formula-II with a hydrogenation catalyst, in water;

(II)

b) isolating the palonosetron free base in solid form using a suitable organic solvent.

3. The process of claim 2, further comprising converting the palonosetron free base in solid form into a pharmaceutically acceptable salt thereof.

4. A process for the preparation of palonosetron free base in crystalline form-G of claim 1, comprising;
    a) providing a solution of palonosetron hydrochloride in a water immiscible organic solvent and water;
    b) treating the solution with a base;
    c) concentrating the water immiscible organic solvent; and
    d) crystallizing the resultant residue in a suitable organic solvent.

5. The process of claim 4, wherein the water immiscible organic solvent is dichloromethane, toluene, or ethyl acetate.

6. The process of claim 5, wherein the crystallizing solvent is methanol, ethyl acetate, water and mixtures thereof.

7. A process for the preparation of palonosetron hydrochloride, comprising:
    a) providing a solution of palonosetron free base in solid form obtained from the process of claim 2;
    b) treating the solution in a) with an aqueous or an anhydrous hydrochloric acid,
    c) isolating the palonosetron hydrochloride.

8. The palonosetron free base in solid crystalline form-G of claim 1, in form of a hydrochloride salt and, having less than about 0.11% of 2-(1-azabicyclo[2.2.2]oct-3-yl)-2,4,5,6-tetrahydro-1H-benz[de]isoquinolin-1-one of formula-II, as determined by high performance liquid chromatography

* * * * *